(12) United States Patent
Ghesu et al.

(10) Patent No.: US 11,717,233 B2
(45) Date of Patent: Aug. 8, 2023

(54) ASSESSMENT OF ABNORMALITY PATTERNS ASSOCIATED WITH COVID-19 FROM X-RAY IMAGES

(71) Applicant: Siemens Healthcare GmbH, Erlangen (DE)

(72) Inventors: Florin-Cristian Ghesu, Princeton, NJ (US); Siqi Liu, Princeton, NJ (US); Awais Mansoor, Potomac, MD (US); Sasa Grbic, Plainsboro, NJ (US); Sebastian Vogt, Monument, CO (US); Dorin Comaniciu, Princeton Junction, NJ (US); Ruhan Sa, Monmouth Junction, NJ (US); Zhoubing Xu, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 423 days.

(21) Appl. No.: 16/947,149

(22) Filed: Jul. 21, 2020

(65) Prior Publication Data

US 2022/0022818 A1 Jan. 27, 2022

(51) Int. Cl.
*A61B 5/00* (2006.01)
*G06T 7/62* (2017.01)
(Continued)

(52) U.S. Cl.
CPC .......... *A61B 5/7275* (2013.01); *A61B 5/7267* (2013.01); *A61B 6/032* (2013.01); *A61B 6/50* (2013.01); *G06F 18/214* (2023.01); *G06T 7/0012* (2013.01); *G06T 7/11* (2017.01); *G06T 7/62* (2017.01); *G16H 30/40* (2018.01);
(Continued)

(58) Field of Classification Search
None
See application file for complete search history.

(56) References Cited

U.S. PATENT DOCUMENTS

| 10,691,980 | B1 | 6/2020 | Guendel et al. |
| 2019/0259153 | A1* | 8/2019 | Zhang .................... G06V 10/82 |
| 2022/0157459 | A1* | 5/2022 | Siewerdsen ............ G06N 5/003 |

OTHER PUBLICATIONS

Li et al., "From community-acquired pneumonia to COVID-19: a deep learning-based method for quantitative analysis of COVID-19 on thick-section CT scans," (Jul. 18, 2020) European Radiology (2020) 30:6828-6837. (Year: 2020).*

(Continued)

*Primary Examiner* — Joel Lamprecht
*Assistant Examiner* — Ashish S Jasani

(57) ABSTRACT

Systems and methods for assessing a disease are provided. An input medical image in a first modality is received. Lungs are segmented from the input medical image using a trained lung segmentation network and abnormality patterns associated with the disease are segmented from the input medical image using a trained abnormality pattern segmentation network. The trained lung segmentation network and the trained abnormality pattern segmentation network are trained based on 1) synthesized images in the first modality generated from training images in a second modality and 2) target segmentation masks for the synthesized images generated from training segmentation masks for the training images. An assessment of the disease is determined based on the segmented lungs and the segmented abnormality patterns.

24 Claims, 12 Drawing Sheets

(51) Int. Cl.
  *G06T 7/11* (2017.01)
  *G16H 50/20* (2018.01)
  *G16H 30/40* (2018.01)
  *A61B 6/03* (2006.01)
  *A61B 6/00* (2006.01)
  *G06T 7/00* (2017.01)
  *G06F 18/214* (2023.01)
(52) U.S. Cl.
  CPC ... *G16H 50/20* (2018.01); *G06T 2207/10081* (2013.01); *G06T 2207/10116* (2013.01); *G06T 2207/20081* (2013.01); *G06T 2207/20084* (2013.01); *G06T 2207/20221* (2013.01); *G06T 2207/30061* (2013.01); *G06V 2201/031* (2022.01)

(56) References Cited

OTHER PUBLICATIONS

Extended European Search Report (EESR) dated Dec. 17, 2021 in corresponding European patent application No. 21186323.8.
Gozes, O., et al.; "Lung structures enhancement in chest radiographs via ct based fcnn training." Image Analysis for Moving Organ, Breast, and Thoracic Images. Springer, Cham, 2018. 147-158.
Shi, F., et al. "Large-scale screening of covid-19 from community acquired pneumonia using infection size-aware classification (2020)." arXiv preprint arXiv:2003.09860 (2003).
Barbosa Jr., E., et al. "Automated Detection and Quantification of COVID-19 Airspace Disease on Chest Radiographs: A Novel Approach Achieving Expert Radiologist-Level Performance Using a Deep Convolutional Neural Network Trained on Digital Reconstructed Radiographs From Computed Tomography-Derived Ground Truth " Investigative radiology (2021).
Zhang, Y., et al.; "Task driven generative modeling for unsupervised domain adaptation: Application to x-ray image segmentation." International Conference on Medical Image Computing and Computer-Assisted Intervention. Springer, Cham, 2018.
Rubin et al., "The role of chest imaging in patient management during the COVID-19 pandemic: a multinational consensus statement from the Fleischner Society", Radiology, Chest, Apr. 2020, 24 pgs.
Murphy et al., "COVID-19 on the chest radiograph: A multi-reader evaluation of an AI system", Radiology, May 2020, 201874, 21 pgs.
Irvin et al., "Chexpert: A large chest radiograph dataset with uncertainty labels and expert comparison", Proceedings of the AAAI Conference on Artificial Intelligence, Jan. 2019, vol. 33, 2019, pp. 590-597.
Singh et al., "Deep learning in chest radiography: detection of findings and presence of change", PloS ONE, Oct. 2018, vol. 13, No. 10, pp. 1-12.
Hwang et al., "Development and validation of a deep learning-based automated detection algorithm for major thoracic diseases on chest radiographs", JAMA Network Open 2.3, Mar. 22, 2019, e191095, pp. 1-13.
Ghesu et al., "Quantifying and leveraging classification uncertainty for chest radiograph assessment", International Conference on Medical Image Computing and Computer-Assisted Intervention, arXiv:1906.07775v1 [cs.CV] Jun. 18, 2019, pp. 1-9.
Lakshminarayanan et al., "Simple and scalable predictive uncertainty estimation using deep ensembles", Advances in Neural Information Processing Systems, Dec. 2017, pp. 1-13.
Eisenhuber et al., "Bedside chest radiography", Respiratory Care, Mar. 2012, vol. 57, No. 3, pp. 427-443.
Koo et al., "Radiographic and CT features of viral pneumonia", Radiographics, May-Jun. 2018, pp. 719-739.
Ranney et al., "Critical supply shortages—the need for ventilators and personal protective equipment during the Covid-19 pandemic", New England Journal of Medicine, Apr. 30, 2020, vol. 382, No. 18, pp. e41(1)-e41(3).
Smithuis, "Lung disease four-pattern approach", Radiology Assistant: Lung Disease, Feb. 1, 2014, pp. 1-63.
Moturu et al., "Creation of Synthetic X-Rays to Train a Neural Network to Detect Lung Cancer", Department of Computer Science, University of Toronto, Aug. 2018, pp. 1-16.
U.S. Appl. No. 15/929,427, filed May 1, 2020, 30 pgs.
U.S. Appl. No. 16/837,979, filed Apr. 1, 2020, 32 pgs.

\* cited by examiner

ASSESSMENT OF ABNORMALITY PATTERNS ASSOCIATED WITH COVID-19 FROM X-RAY IMAGES

TECHNICAL FIELD

The present invention relates generally to the assessment of abnormality patterns associated with a disease from x-ray images, and in particular to the assessment of abnormality patterns associated with COVID-19 (coronavirus disease 2019) from x-ray images using machine learning networks trained based on DRRs (digitally reconstructed radiographs) and ground truths derived from CT (computed tomography).

BACKGROUND

COVID-19 (coronavirus disease 2019) is an infectious disease caused by the severe-acute respiratory symptom coronavirus 2 (SARS-Cov2). Common symptoms of COVID-19 include fever, cough, and difficulty breathing. In the majority of cases, patients infected with COVID-19 experience mild to moderate symptoms that do not require hospitalization. However, in severe cases, COVID-19 can cause pneumonia, severe acute respiratory syndrome, multiple organ failure, and death.

In the current clinical workflow, diagnostic imaging is typically performed on patients suspected of, or confirmed as, having COVID-19 to visualize the extent and severity of COVID-19 in the lungs and other organs. One form of diagnostic imaging is CT (computed tomography) imaging, which provides high-resolution 3D images that may be used for assessing COVID-19. However, many clinical sites do not have the resources to acquire such CT imaging or to disinfect the CT imaging scanner after acquiring the CT imaging. Another form of diagnostic imaging is x-ray imaging, which is relatively inexpensive to acquire and more readily available as compared to CT imaging. However, x-ray imaging is inherently ambiguous due to its 2D nature, resulting in inconsistent readings by radiologists.

Existing machine learning based approaches have been proposed for classifying abnormality patterns in x-ray imaging. Typically, the underlying machine learning model is trained based on x-ray training images annotated by a radiologist. However, performance of machine learning models trained on manually annotated x-ray training images is limited due to the uncertainty in the accuracy and consistency of the annotations in view of the ambiguity of the x-ray images.

BRIEF SUMMARY OF THE INVENTION

In accordance with one or more embodiments, systems and methods for assessing a disease are provided. An input medical image in a first modality is received. Lungs are segmented from the input medical image using a trained lung segmentation network and abnormality patterns associated with the disease are segmented from the input medical image using a trained abnormality pattern segmentation network. The trained lung segmentation network and the trained abnormality pattern segmentation network are trained based on 1) synthesized images in the first modality generated from training images in a second modality and 2) target segmentation masks for the synthesized images generated from training segmentation masks for the training images. An assessment of the disease is determined based on the segmented lungs and the segmented abnormality patterns.

In one embodiment, the disease is COVID-19 (coronavirus disease 2019) and the abnormality patterns include at least one of GGO (ground glass opacity), consolidation, and crazy-paving pattern.

In one embodiment, at least one of the lung segmentation network and the abnormality pattern segmentation network is trained by receiving training images of an anatomical object of interest in the second modality and training segmentation masks for the training images, generating synthesized images in the first modality based on the training images, generating target segmentation masks for the synthesized images based on the training segmentation masks, and training the at least one of the lung segmentation network and the abnormality pattern segmentation network based on the synthesized images and the target segmentation masks.

In one embodiment, the target segmentation masks are generated by projecting regions of the training images within their corresponding training segmentation masks to a two dimensional mask and assigning each pixel in the two dimensional mask a value corresponding to a thickness of penetration of the projecting through the anatomical object of interest in the training images for that pixel. The value of each pixel in the two dimensional mask is compared to a threshold value and each pixel in the two dimensional mask is assigned a final value based on the comparing.

In one embodiment, the target segmentation masks are generated by projecting regions of the training images within their corresponding training segmentation masks to a two dimensional mask and assigning each pixel in the two dimensional mask a value corresponding to a sum of intensity values of voxels in the training images that are within the anatomical object of interest and penetrated by the projecting for that pixel. The value of each pixel in the two dimensional mask is compared to a threshold value and each pixel in the two dimensional mask is assigned a final value based on the comparing.

In one embodiment, the assessment of the disease is determined by calculating a percent of affected lung area metric based on an area of the lungs determined from the segmented lungs and an area of the abnormality patterns determined from the segmented abnormality patterns.

In one embodiment, the disease is detected in the input medical image based on the assessment of the disease.

In one embodiment, an evolution of the disease is predicted based on the assessment of the disease and an assessment of the disease determined for a different point in time.

In one embodiment, the first modality is x-ray and the second modality is CT (computed tomography).

These and other advantages of the invention will be apparent to those of ordinary skill in the art by reference to the following detailed description and the accompanying drawings.

DETAILED DESCRIPTION

The present invention generally relates to methods and systems for the assessment of abnormality patterns associated with COVID-19 (coronavirus disease 2019) from x-ray images. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

COVID-19 is an infectious disease that typically presents a wide range of symptoms, ranging from asymptomatic to mild, moderate, severe, and critical symptoms. Diagnostic images of the chest of a patient with COVID-19 may show radiographic abnormality patterns associated with COVID-19. One form of diagnostic imaging is x-ray images or radiographs, which are relatively inexpensive to acquire and are readily available. However, such x-ray images are inherently ambiguous due to their 2D nature, resulting in inconsistent and unreliable annotations of lungs, abnormality patterns, and other anatomical objects of interest in the x-ray images by radiologists. Accordingly, machine learning based systems trained using such manually annotated x-ray images have limited accuracy and performance.

Embodiments described herein provide for the assessment of abnormality patterns associated with COVID-19 from x-ray images using machine learning based segmentation networks to segment the lungs and the abnormality patterns from the x-ray images. Such segmentation networks are trained using synthesized x-ray images generated from 3D CT training images and ground truth target segmentation masks generated from training segmentation masks annotated by a radiologist (or any other user) from the 3D CT training images. It is easier for radiologists to more accurately and consistently annotate the lungs, the abnormality patterns, or any other anatomical object of interest from 3D CT images as compared to x-ray images due to the 3D nature of the 3D CT images. Advantageously, segmentation networks trained using the synthesized x-ray images and the target segmentation masks for the synthesized x-ray images, in accordance with embodiments described herein, segment the lungs and the abnormality patterns from the x-ray images with improved accuracy and performance, and are not limited by ambiguities inherent in x-ray images.

Figure 1:
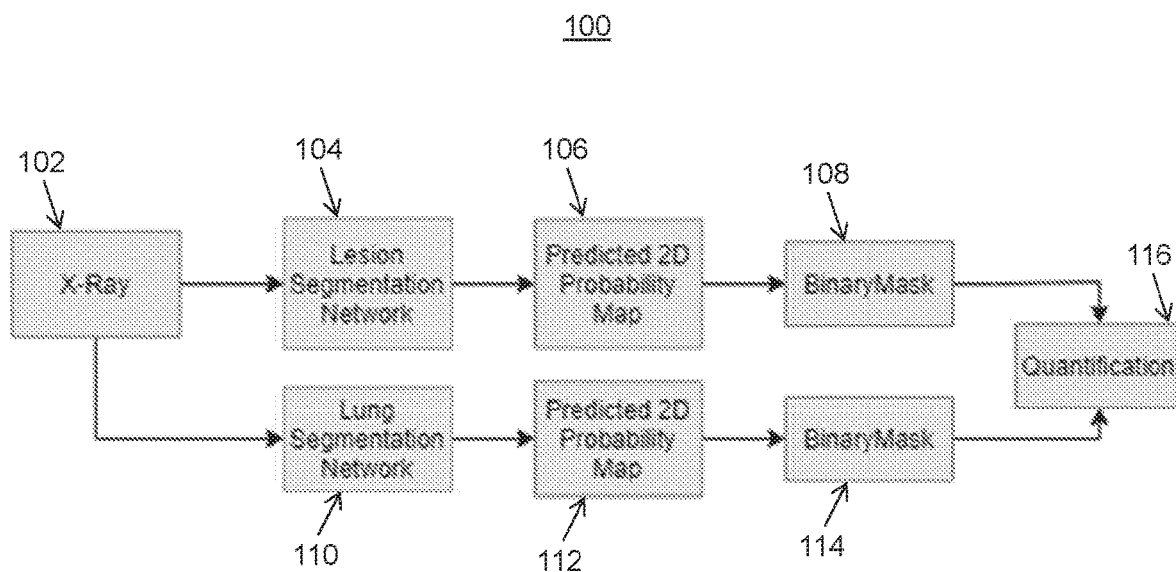
FIG. 1 shows a workflow for assessing a disease in a patient, in accordance with one or more embodiments.
Figure 2:
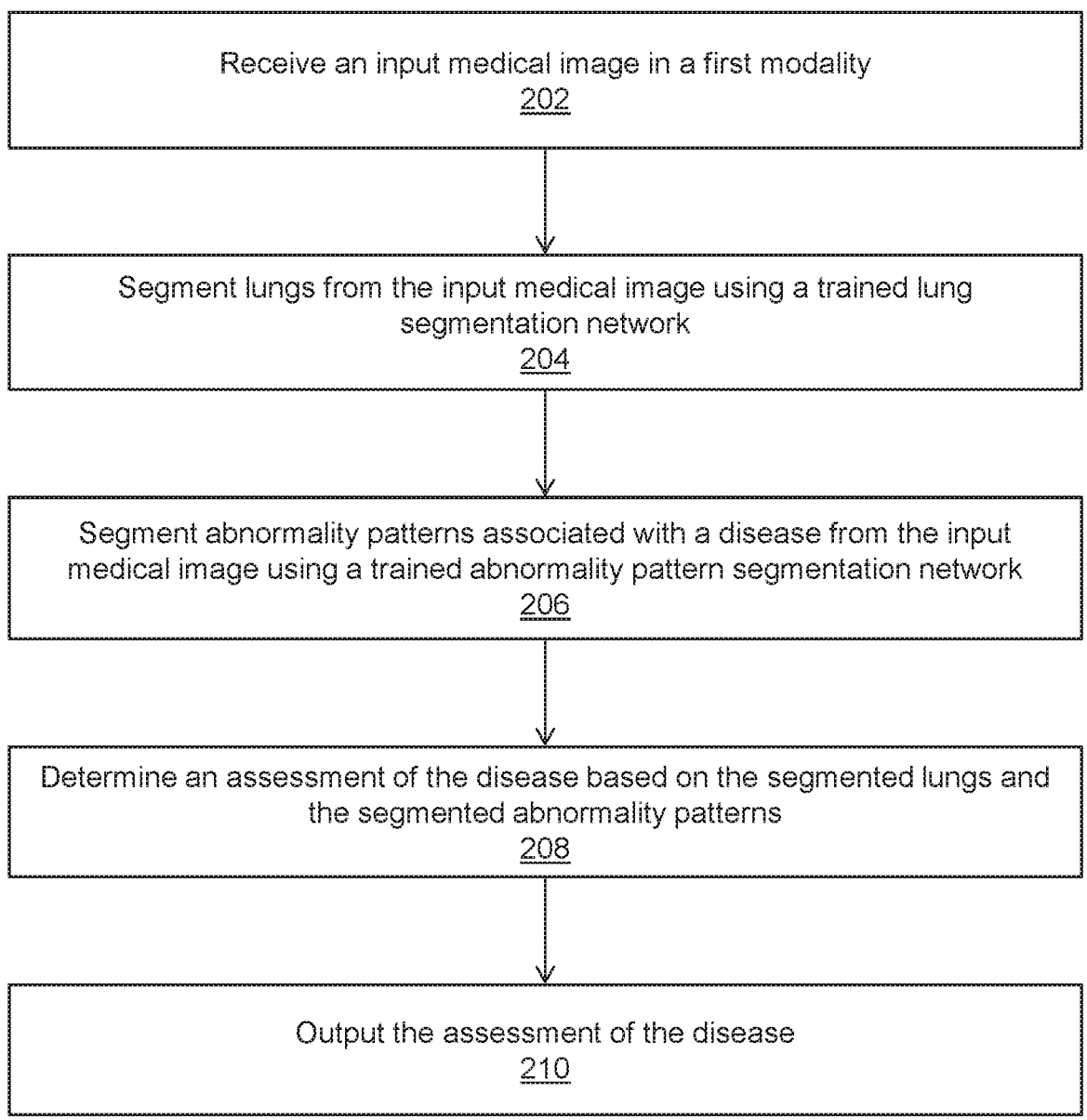
FIG. 2 shows a method for assessing a disease in a patient, in accordance with one or more embodiments.

FIG. 1 is a workflow 100 for assessing a disease in a patient, in accordance with one or more embodiment. FIG. 2 is a method 200 for assessing a disease in a patient, in accordance with one or more embodiments. FIGS. 1 and 2 will be described together. The steps of method 200 may be performed by one or more suitable computing devices, such as computer 1102 of FIG. 11.

At step 202, an input medical image in a first modality is received. The input medical image may be of a chest of a patient suspected of, or confirmed as, having a disease. In one embodiment, the disease is a member of the family of coronaviruses. For example, the disease may be COVID-19. As used herein, COVID-19 includes mutations of the COVID-19 virus (which may be referred to by different terms). However, the disease may include any disease with recognizable abnormality patterns in the lungs, such as, e.g., consolidation, interstitial disease, atelectasis, nodules, masses, decreased density or lucencies, etc. For example, the disease may be other types of viral pneumonia (e.g., influenza, adenovirus, respiratory syncytial virus, SARS (severe acute respiratory syndrome), MERS (Middle East respiratory syndrome), etc.), bacterial pneumonia, fungal pneumonia, mycoplasma pneumonia, or other types of pneumonia or other types of diseases.

The input medical image may depict the lungs of the patient and, possibly, radiographic abnormality patterns associated with the disease in the lungs of the patient. For example, where the disease is COVID-19, the abnormality patterns may include opacities such as, e.g., GGO (ground glass opacity), consolidation, crazy-paving pattern, atelectasis, interlobular septal thickening, pleural effusions, bronchiectasis, halo signs, etc.

In one embodiment, the first modality is 2D x-ray imaging or 2D radiography. For example, the input medical image may be x-ray image 102 of FIG. 1. However, the first modality may be any suitable modality, such as, e.g., CT (computed tomography), MRI (magnetic resonance imaging), US (ultrasound), or any other modality or combination of modalities. The input medical image may comprise 2D images or 3D volumes, and may comprise a single image or a plurality of images (e.g., a sequence of images acquired over time). The input medical image may be received directly from an image acquisition device, such as, e.g., a x-ray scanner, as the input medical image is acquired, or can be received by loading a previously acquired input medical image from a storage or memory of a computer system or receiving the input medical image from a remote computer system.

Figure 6:
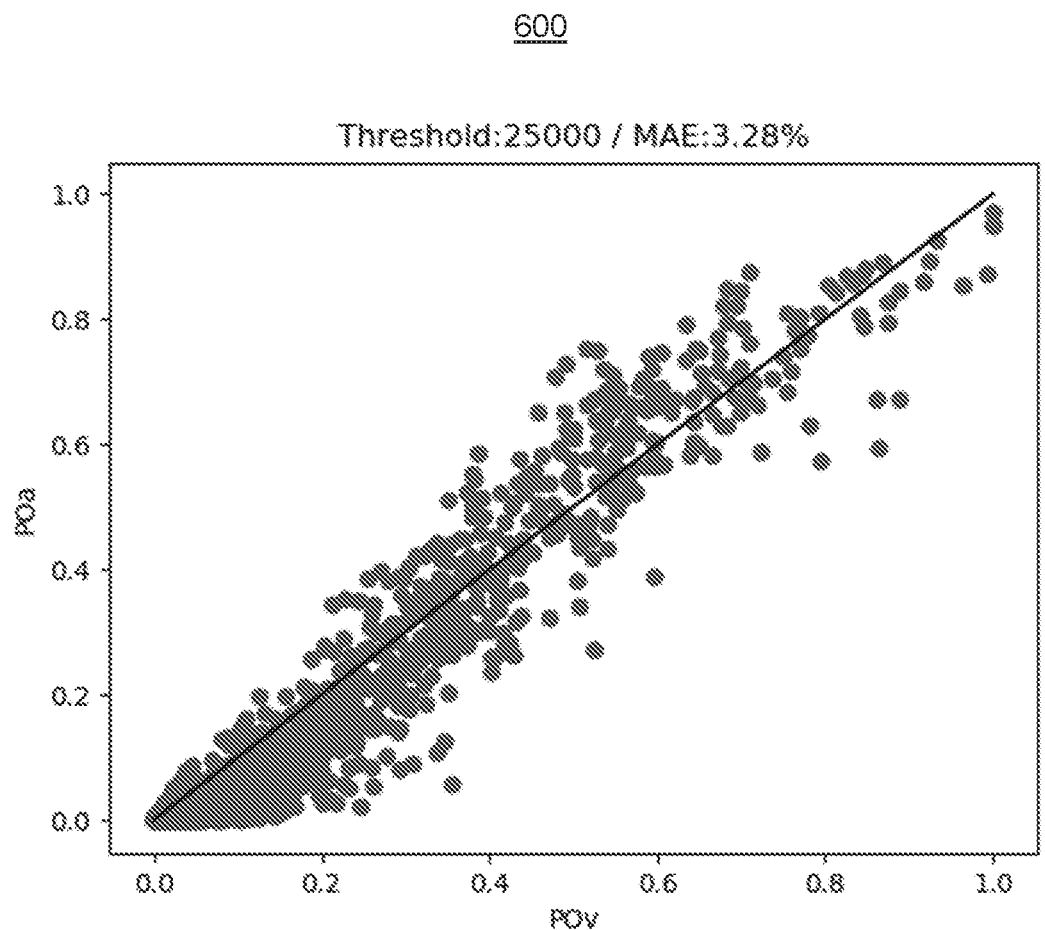
FIG. 6 shows a graph showing a correlation between percentage of affected lung area (POa) and percentage of affected lung volume (POv), in accordance with one or more embodiments.

At step 204, lungs are segmented from the input medical image using a trained lung segmentation network. The lung segmentation network predicts a probability map representing the segmented lungs. The probability map defines a pixel wise probability that each pixel depicts the lungs. The probability map may be represented as a binary mask by comparing the probability for each pixel to a threshold value (e.g., 0.5). The binary mask assigns each pixel a value of, e.g., 0 where the pixel does not depict the lungs and 1 where the pixel depicts the lungs. In one example, the lung segmentation network is lung segmentation network 110 that generates a predicted 2D probability map 112 which is represented as a binary mask 114 in FIG. 1. Exemplary lung segmentations are shown in FIG. 6, described in further detail below.

In one embodiment, the lung segmentation network is an image-to-image CNN (convolutional neural network), however the lung segmentation network may be any suitable machine learning based network. The lung segmentation network is trained during a prior offline or training stage based on 1) synthesized images in the first modality generated from training images in a second modality and 2) target segmentation masks of the lungs for the synthesized images generated from training segmentation masks of the lungs for the training images. In one embodiment, the second modality is 3D CT imaging. However, the second modality may be any suitable modality, such as, e.g., x-ray, MRI, US, or any other modality or combination of modalities, and may include 2D images or 3D volumes. The training of the lung segmentation network is further described below with respect to FIGS. 3 and 4. Once trained, the lung segmentation network is applied, during an online or inference stage, at step 204.

At step 206, abnormality patterns associated with the disease are segmented from the input medical image using a trained abnormality pattern segmentation network. The abnormality pattern segmentation network predicts a probability map representing the segmented abnormality pattern. The probability map defines a pixel wise probability that each pixel depicts the abnormality pattern. The probability map may be represented as a binary mask by comparing the probability for each pixel to a threshold value (e.g., 0.5). The binary mask assigns each pixel a value of, e.g., 0 where the pixel does not depict the abnormality pattern and 1 where the pixel depicts the abnormality pattern. In one example, the abnormality pattern segmentation network is lesion segmentation network 104 that generates a predicted 2D probability map 106 which is represented as a binary mask 108 in FIG. 1.

In one embodiment, the abnormality pattern segmentation network is an image-to-image CNN, however the abnormality pattern segmentation network may be any suitable machine learning based network. The abnormality pattern segmentation network is trained during a prior offline or training stage based on 1) synthesized images in the first modality generated from training images in the second modality and 2) target segmentation masks of the abnormality patterns for the synthesized images generated from training segmentation masks of the abnormality patterns for the training images. The training of the abnormality pattern segmentation network is further described below with respect to FIGS. 3 and 4. Once trained, the abnormality pattern segmentation network is applied, during an online or inference stage, at step 206.

At step 208, an assessment of the disease is determined based on the segmented lungs and the segmented abnormality patterns. In one embodiment, the assessment of the disease is determined by computing a quantitative metric quantifying the disease. For example, the quantitative metric may be quantification 116 of the disease determined from binary mask 108 of lesions and binary mask 114 of the lungs in FIG. 1.

In one embodiment, the quantitative metric is a percentage of affected lung area (POa) calculated as the total percent area of the lungs that is affected by the disease, as defined in Equation (1).

$$POa = 100 \times \frac{\text{area of the abnormality patterns in the lungs}}{\text{area of the lungs}} \quad \text{Equation (1)}$$

where the area of the abnormality patterns in the lungs is determined as the area of the segmented abnormality patterns and the area of the lungs is determined as the area of the segmented lungs. The quantitative metric may be any other metric suitable for quantifying the disease, such as, e.g., a LSS (lung severity score) calculated, for each lobe of the lungs, as the total percent area of a lobe that is affected by the disease.

At step 210, the assessment of the disease is output. For example, the assessment of the disease can be output by displaying the assessment of the disease on a display device of a computer system, storing the assessment of the disease on a memory or storage of a computer system, or by transmitting the assessment of the disease to a remote computer system.

Embodiments described herein provide for the assessment of the disease using segmentation networks trained using synthesized x-ray images and ground truth target segmentation masks generated from annotated CT training images, which are relatively easier to annotate by a radiologist as compared to 2D x-ray images due to the 3D nature of the CT training images and the inherent loss of anatomical detail in 2D projection images caused by tissue and anatomical overlap. The segmentation networks, in accordance with embodiments described herein, are not trained solely based annotated x-ray images, thereby avoiding the inherent uncertainty of the x-ray images. Advantageously, embodiments described herein provide for the segmentation of the lungs and the abnormality patterns of the disease with improved accuracy and performance, thereby providing for assessment of the disease with improved accuracy.

In one embodiment, an ensemble (i.e., a plurality) of segmentation networks may be applied to model uncertainty. Given the limited visibility of volumetric structures when projecting 3D CT images to DRR images (digitally reconstructed radiographs), both the mapping between the DRR image (synthesized x-ray image) and the target lung segmentation mask and the mapping between the DRR image and the target abnormality pattern segmentation mask are subject to intrinsic uncertainty. Using a standard training procedure which disregards such uncertainty, a per-sample bias in the estimation of the lesion area can be expected. In one embodiment, an ensemble of segmentation networks are utilized to model the uncertainty, either during the training stage or the testing stage. For instance, a plurality of segmentation networks may be trained on the same training data and the predictions from each of the segmentation networks may be averaged to thereby account for the uncertainty.

In one embodiment, a machine learning based detection network may additionally be applied for detecting the disease (e.g., COVID-19) in the input medical image. In one embodiment, the detection may be formulated as a mapping from the feature space of the segmentation networks, as well as the lung and abnormality pattern segmentations, to a disease score or probability measure of the disease using an image-wise disease classifier or detector (e.g., bounding boxes). In another embodiments, detection may be performed by regressing using extracted quantitative biomarkers (e.g., percentage of opacity). Additional clinical data may also be input into the detection network. The additional clinical data may include patient data (e.g., demographics), clinical data, genetic data, laboratory data, etc.

In one embodiment, high-quality annotations of CT images may be utilized to detect and quantify temporal changes in x-ray images. Detecting and quantifying the temporal changes may include analyzing the evolution of existing lesions (e.g., capturing an increase in the size of pulmonary nodules), detecting and quantifying new lesions, and tracking geometric changes of organs.

In one embodiment, evolution or progression of the disease may be predicted. Based on the assessment of the disease and, possibly, the detection of the disease (using a detection network) determined at a plurality of points in time, a wide range of measurements may be extracted, such as, e.g., POa, location and spread of lesions, symmetry, etc. Aggregated over time through follow-up radiographs, such measurements may be used to predict the evolution of the disease, allowing for early detection of trends in the patient's condition. For example, one may predict the severity of the disease, assess the need for future intubation and the projected period of intubation, etc. Such prognostic information enables more effective management of the disease and the patient. In addition, in low resource locations, this information may enable better management of valuable or scarce resources, such as, e.g., hospital beds, ventilators, etc. In one embodiment, the evolution of the disease is predicted by generating quantitative biomarkers (e.g., percentage of opacity) from the x-ray images at each of the plurality of points in time. The biomarkers may be recorded in a database and tracked over different longitudinal studies to understand the effectiveness of the different treatments. In another embodiment, the spatial locations of detections and segmentations, determined according to embodiments described herein, can also be used to track expansion or shrinkage of lesions or new or disappeared lesions in the same region using image registration techniques. Since embodiments described herein train networks using CT images with higher reading confidence, the disease tracking accuracy is superior to systems trained on x-ray annotations alone.

In one embodiment, the disease is not limited to lung diseases. Embodiments described herein may be extended for the assessment of any disease that affects any organ for which radiographic imaging is used, which may be correlated to higher level imaging modalities (e.g., CT or MR). For example, embodiments described herein may be extended to detect and monitor abdominal cancers (e.g., colon cancer, pancreatic cancer, hepatocellular carcinoma, renal cell carcinoma, etc.), pathological abnormalities of the gallbladder, liver, or pancreas, etc.

Figure 3:
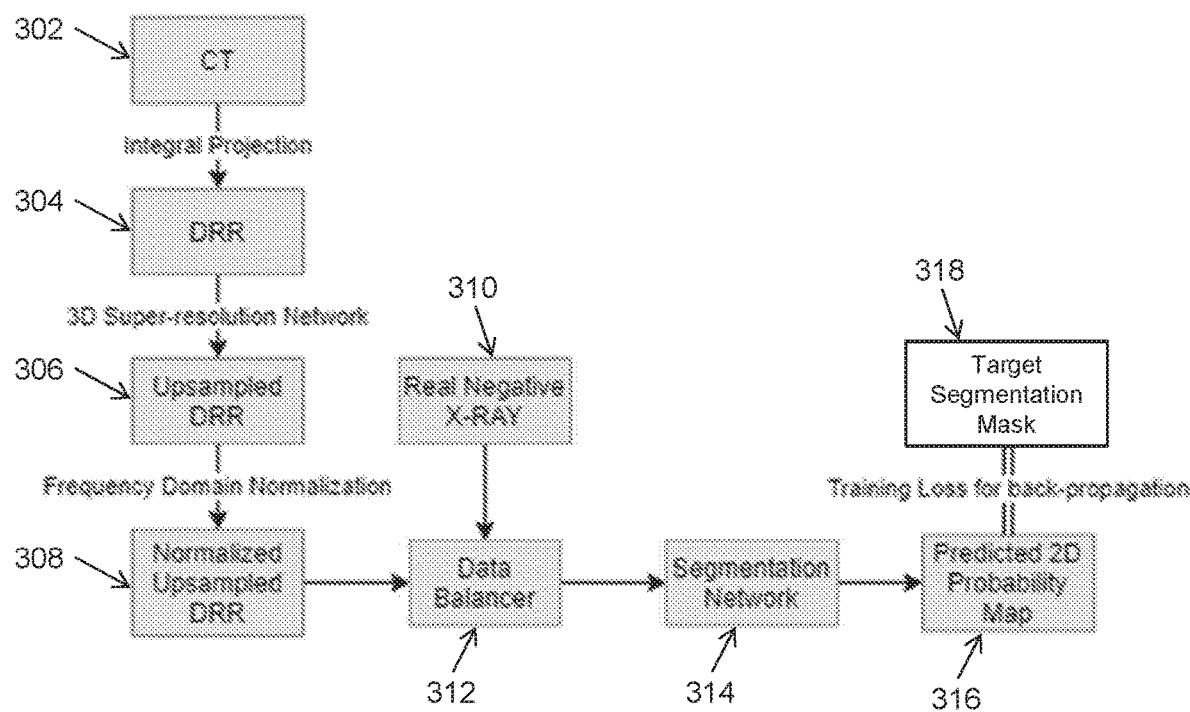
FIG. 3 shows a workflow for training a segmentation network for segmenting an anatomical object of interest based on CT training images, in accordance with one or more embodiments.
Figure 4:
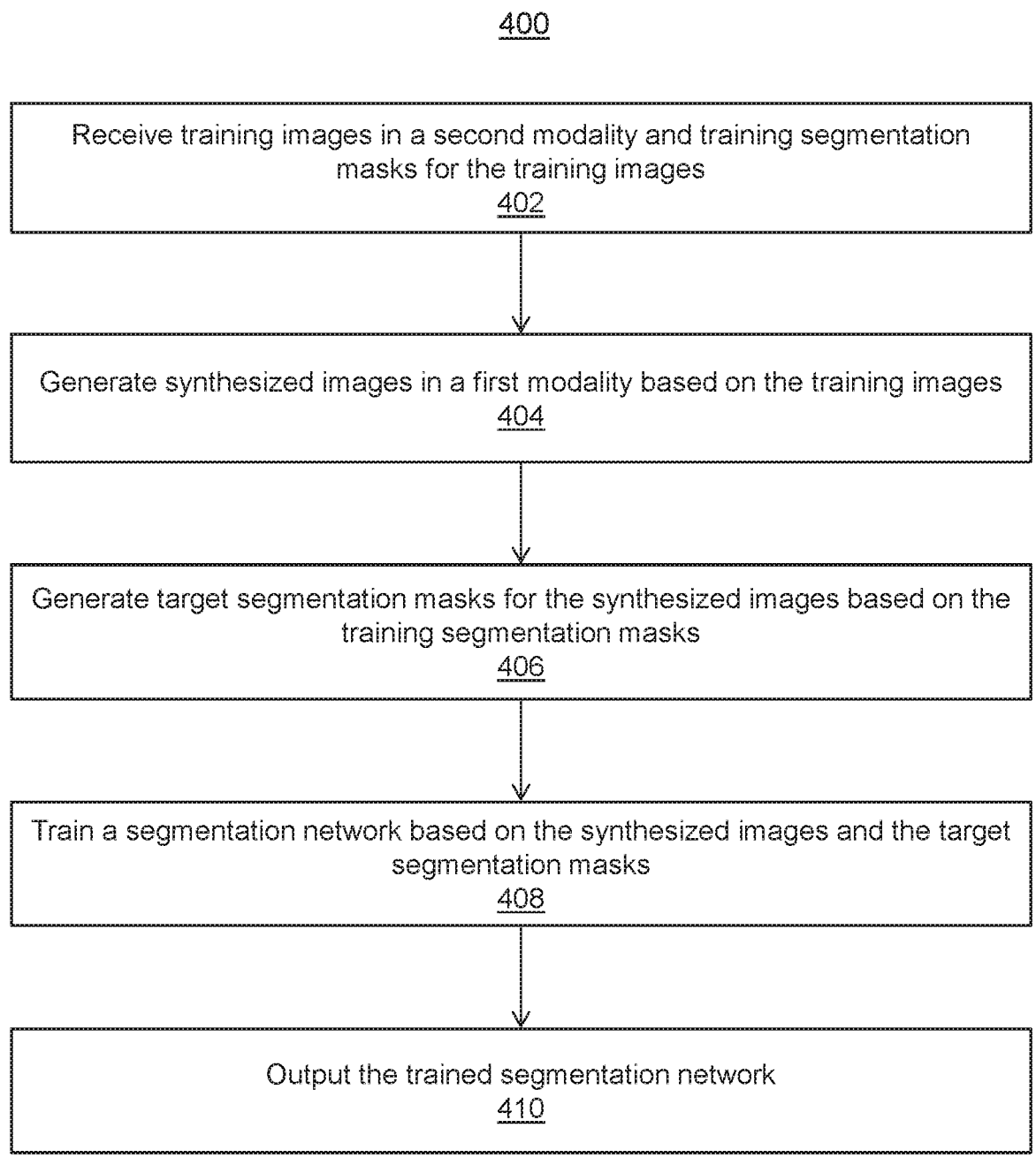
FIG. 4 shows a method for training a segmentation network for segmenting an anatomical object of interest from a medical image, in accordance with one or more embodiments.

FIG. 3 shows a workflow 300 for training a segmentation network for segmenting an anatomical object of interest based on CT training images, in accordance with one or more embodiments. FIG. 4 shows a method 400 for training a segmentation network for segmenting an anatomical object of interest from a medical image, in accordance with one or more embodiments. FIG. 3 and FIG. 4 will be described together. The steps of method 400 may be performed by one or more suitable computing devices, such as computer 1102 of FIG. 11.

The steps of workflow 300 and method 400 are performed during an offline or training stage to train a segmentation network for segmenting an anatomical object of interest from a medical image. The steps of workflow 300 and method 400 may be performed any number of iterations to separately train segmentation networks for segmenting different anatomical objects of interest from medical images. Once trained, the segmentation network is applied during an online or testing stage. In one embodiment, the steps of workflow 300 and method 400 may be repeatedly performed to train the lung segmentation network applied at step 204 of FIG. 2 during a first iteration and to train the abnormality pattern segmentation network applied at step 206 of FIG. 2 during a second iteration.

At step 402, training images in a second modality and training segmentation masks for the training images are received. The training images depict anatomical objects of interest that the segmentation network is being trained to segment. In one embodiment, the anatomical objects of interest include the lungs of the patient and, possibly, abnormality patterns associated with a disease in the lungs of the patient. As discussed above with respect to FIG. 2, in one embodiment, the second modality is 3D CT imaging. However, the second modality may be any suitable modality or combination of modalities. In one example, the training images and the segmentation masks may be annotated CT images 302 in FIG. 3.

The training segmentation masks for the training images identify the anatomical object of interest in the training images that the segmentation network is being trained to segment. The training segmentation masks are manually annotated in the training images by a radiologist. In one embodiment, e.g., where the training images are 3D CT training images, the training segmentation masks are 3D training segmentation masks. Manual annotation of the 3D CT training images to generate the 3D training segmentation masks by the radiologist is easier perform as compared to 2D x-ray images due to the 3D nature of 3D CT images.

The training images and the training segmentation masks may be received by loading the training images and the training segmentation masks from a storage or memory of a computer system or receiving the training images and the training segmentation masks from a remote computer system.

At step 404, synthesized images in a first modality are generated based on the training images. As discussed above with respect to FIG. 2, in one embodiment, the first modality is 2D x-ray imaging. However, the first modality may be any suitable modality or combination of modalities. The synthesized images may be generated by translating the training images from the second modality to the first modality using any suitable technique.

In one embodiment, as shown in FIG. 3, synthesized 2D x-ray images are generated from 3D CT training images 302 by first performing integral projection to project the 3D CT training images 302 to 2D DRR (digitally reconstructed radiograph) images 304 using Beer's law to approximate the physical x-ray travelling through tissue. Typically, x-ray images have a high resolution. However, the projected DRR images 304 have a relatively lower resolution. Accordingly, DRR images 304 are upsampled to generate upsampled DRR images 306 using a 3D super-resolution network. Upsampled DRR images 306 then undergo frequency domain normalization to normalize intensities of the upsampled DRR images 306 to generate normalized upsampled DRR images 308. The frequency domain normalization addresses the limited contrast and high noise in the upsampled DRR images 306 resulting from the projection of the 3D CT training images 302 to 2D DRR images 304. The normalized upsampled DRR images 308 represent the synthesized x-ray images.

It should be understood that the synthesized images may be generated using any other suitable technique. For example, the synthesized images may be generated from the training images using a machine learning based network, such as, e.g., a generative adversarial network.

At step 406, target segmentation masks for the synthesized images are generated based on the training segmentation masks. The target segmentation masks represent the ground truth identification of the target anatomical object of interest in the synthesized images.

Figure 5:
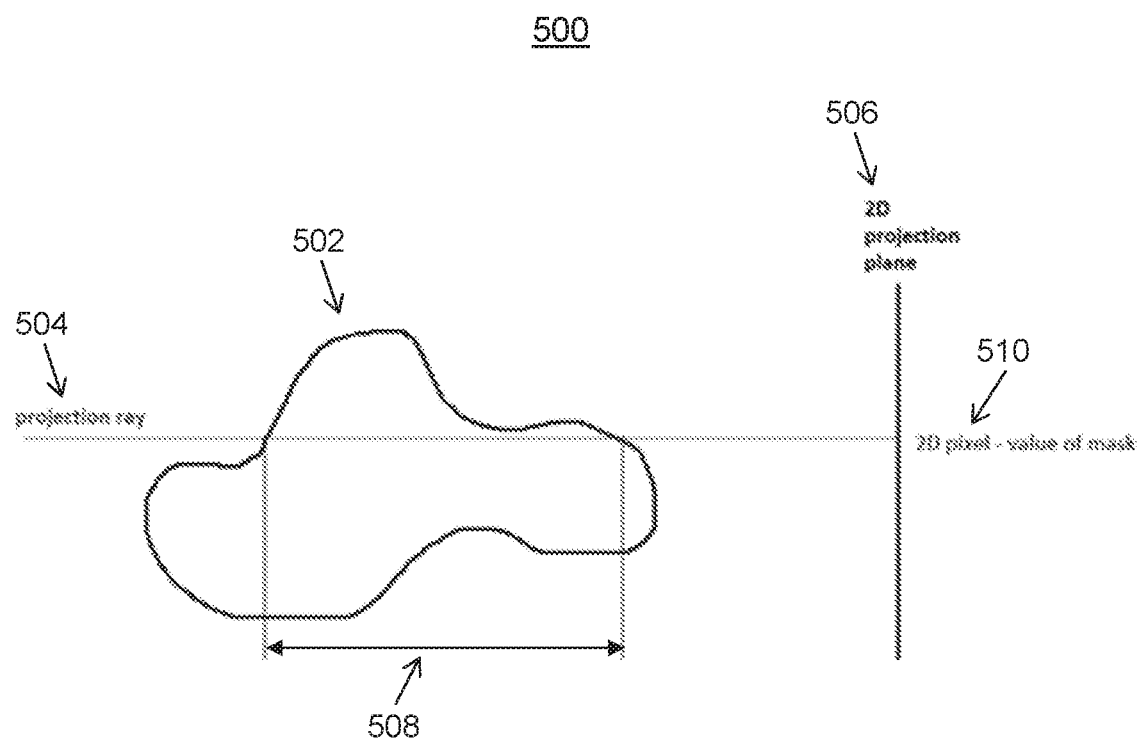
FIG. 5 shows a diagram illustrating calculation of pixel values for generating a thickness mask or an intensity mask, in accordance with one or more embodiments.

In one embodiment, for example, where the training segmentation masks are 3D training segmentation masks of anatomical objects of interest for the 3D CT training images, regions of the 3D CT training images within their corresponding 3D training segmentation masks are projected to 2D masks (e.g., using Beer's law). Each pixel in the 2D masks is assigned a value corresponding to the thickness or depth (e.g., in millimeters) of penetration of the projected x-ray through the anatomical object of interest in the 3D CT training images for that pixel to generate the 2D target segmentation masks. Accordingly, the 2D target segmentation masks generated according to this embodiment may be thought of as "thickness masks." The thickness masks are more correlated to geometric information in the 3D CT training images. Referring for a moment to FIG. 5, diagram 500 illustrates calculation of pixel values of a 2D target segmentation mask, in accordance with one or more embodiment. As shown in diagram 500, anatomical object 502 (e.g., lungs or abnormality patterns) in a 3D CT image is projected to a 2D projection plane 506 according to projection ray 504. Projection ray 504 is within anatomical object 502 at region 508. In accordance with one embodiment, the value assigned to pixel 510 of 2D projection plane 506 is determined as the distance of projection ray 504 within region 508 to form a thickness mask.

Returning back to step 406 of FIG. 4, in another embodiment, for example, where the training segmentation masks are 3D training segmentation masks of anatomical objects of interest for the 3D CT training images, regions of the 3D CT training images within their corresponding 3D training segmentation mask are projected to 2D masks (e.g., using Beer's law). Each pixel in the 2D target segmentation masks is assigned a value corresponding to the sum of the intensity values of voxels in the 3D CT training images that are within the anatomical object of interest and penetrated by the projection of the x-ray for that pixel to generate the 2D target segmentation masks. Accordingly, the 2D target segmentation masks generated according to this embodiment may be thought of as a "intensity masks." The intensity masks are more correlated to visibility in the 3D CT training images. Referring for a moment to FIG. 5, in accordance with one embodiment, the value assigned to pixel 510 of 2D projection plane 506 is determined as the sum of intensity values of along projection ray 504 within region 508 to form an intensity mask.

Other techniques for generating the target segmentation masks are also contemplated.

In one embodiment, the thickness masks and/or the intensity masks are thresholded to minimize the numerical discrepancy between the quantification metrics that would be derived from 2D synthesized x-ray images and corresponding 3D CT images. For example, where the quantification metric is the POa, the threshold value may be determined to minimize the absolute error between the percentage of affected lung volume (POv) for 3D CT images and the POa for 2D synthesized x-ray images. The thickness masks and/or the intensity masks are thresholded by comparing each pixel of the 2D thickness masks and/or the intensity masks with the threshold value and assigning that pixel a final value of 0 or a 1 based on the comparison (e.g., the pixel is assigned a 0 if the value of the pixel in the thickness masks and/or the intensity masks does not satisfy the threshold value and a 1 if the value of the pixel does satisfy the threshold value). FIG. 6 shows a graph 600 showing correlation between POa and POv using a threshold value of 25,000 on intensity masks, in accordance with one or more embodiments. The threshold value of 25,000 achieves a (MAE) mean absolute error of 3.28%.

At step 408, a segmentation network is trained based on the synthesized images and the target segmentation masks. The segmentation network is trained to learn a mapping between the synthesized images and the target segmentation masks. In one embodiment, the segmentation network is an image-to-image CNN. However, the segmentation network may be any suitable machine learning based network.

In one embodiment, the segmentation network is initially pre-trained using a large-scale natural image dataset for parameter initialization. Alternatively, large pools of annotated x-ray images may be used for the pre-training. The segmentation network is then trained using a combination of positive synthesized x-ray images, negative synthesized x-ray images, and real negative x-ray images confirmed by a user. The real negative x-ray images are real x-ray images that do not depict abnormality patterns associated with the disease. Real positive x-ray images are not used for training the segmentation network due to the difficultly in accurately and consistently annotating the abnormality patterns in x-ray images in view of their inherent ambiguity. The positive synthesized x-ray images, negative synthesized x-ray images, and real negative x-ray images may be randomly selected or selected according to a predefined weighting scheme to balance the images. The segmentation network may be optimized using pixelwise loss (e.g., cross-entropy loss) or intersection-based loss (e.g., soft dice loss). The final parameter and the segmentation network model are selected based on a validation dataset (e.g., reserved as 10% of the training data).

In one example, as shown in FIG. 3, segmentation network 314 is trained based on a combination of positive and negative normalized upsampled DRR images 308 and real negative x-ray images 310 (as well as their associated target segmentation masks). The images are positive and negative normalized upsampled DRR images 308 and real negative x-ray images 310 are selected by data balancer 312 to balance the images. Segmentation network 314 is trained according to the training loss for backpropagation to optimize (e.g., minimize) the difference between predicted 2D probability maps 316 and target segmentation masks 318.

At step 410, the trained segmentation network is output. For example, the trained segmentation network can be output by storing the trained segmentation network on a memory or storage of a computer system, or by transmitting the trained segmentation network to a remote computer system for use during an online or testing stage (e.g., at steps 204 and 206 of FIG. 2).

Figure 7:
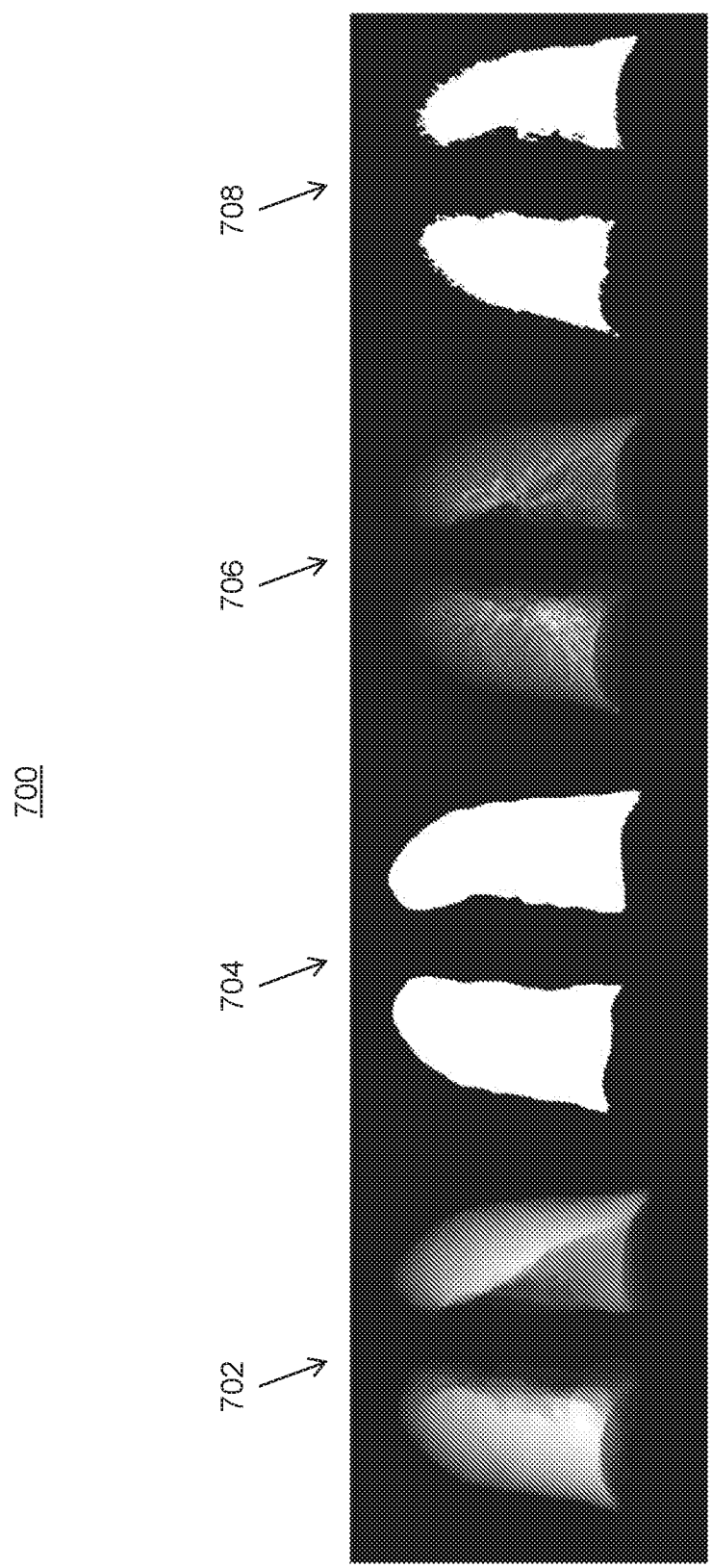
FIG. 7 shows exemplary images of lung segmentations segmented by a segmentation network trained in accordance with one or more embodiments.

FIG. 7 shows exemplary images 700 of lung segmentations segmented by the segmentation network trained in accordance with one or more embodiments described herein. Image 702 shows a lung segmentation according to a thickness mask. Image 704 shows a thresholded lung segmentation mask according to a thickness mask. Image 706 shows a lung segmentation according to an intensity mask. Image 708 shows a thresholded lung segmentation according to an intensity mask.

Figure 8:
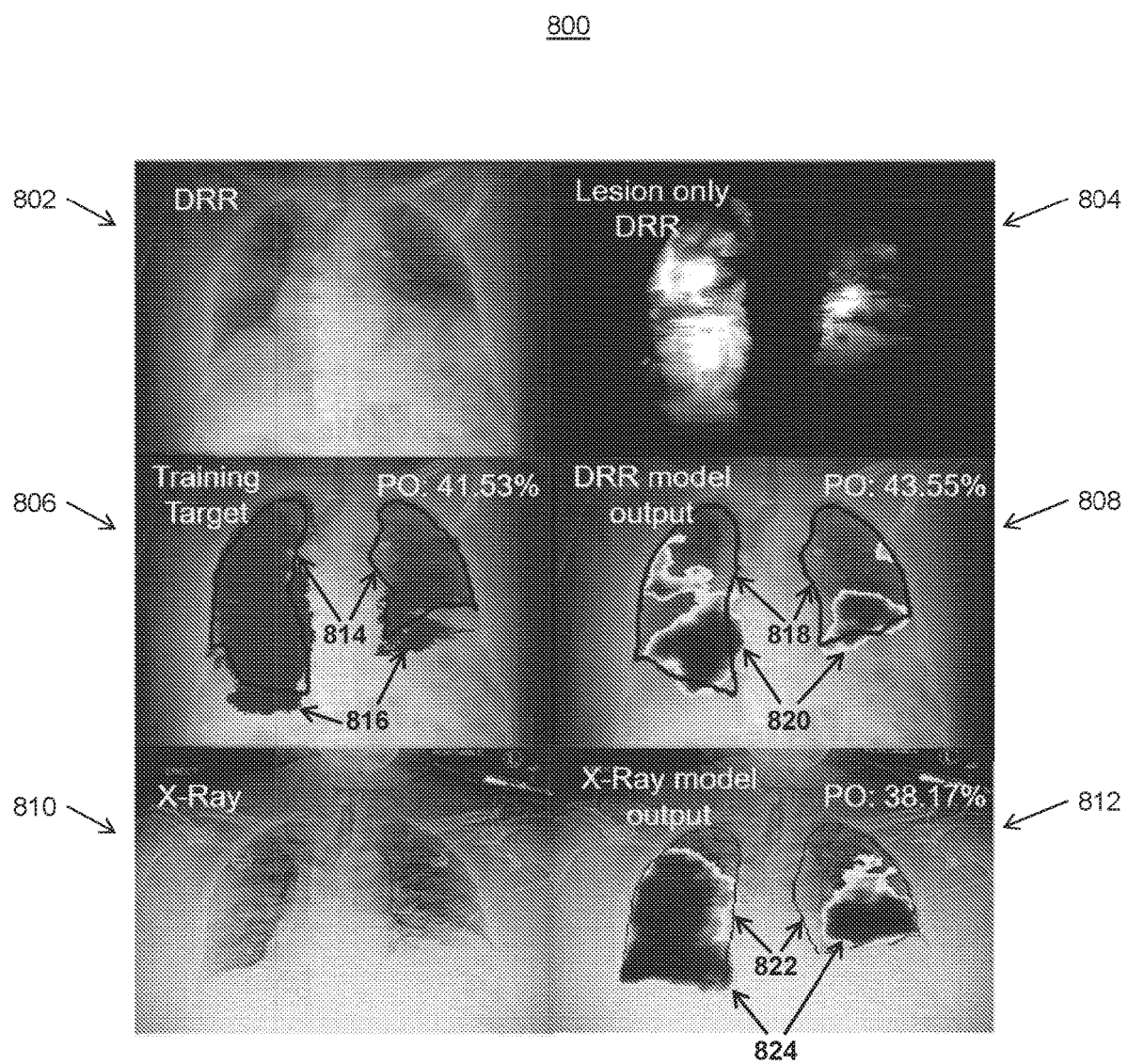
FIG. 8 shows various images depicting the assessment of COVID-19 (coronavirus disease 2019), in accordance with one or more embodiments

FIG. 8 shows various images 800 depicting the assessment of COVID-19, in accordance with one or more embodiments. Image 802 is a DRR image, representing a synthesized x-ray image, that is input into lung and abnormality pattern segmentation networks. Image 804 depicts segmentation of abnormality patterns in DRR image 802 (a lesion only DRR) using an intensity mask. Image 806 shows a target lung segmentation mask 814 (shown as outlined regions) and target abnormality pattern segmentation mask 816 (shown as shaded regions) overlaid on DRR image 802. Image 808 shows an output of an assessment of COVID-19 (DRR model output) depicting predicted segmentations for the lungs 818 (shown as outlined regions) and the abnormality patterns 820 (shown as shaded regions) overlaid on DRR image 802, which results in a POa of 43.55%. Image 810 shows a real x-ray image and image 812 shows an output of an assessment of COVID-19 (x-ray model output) depicting predicted segmentations for the lungs 822 (shown as outlined regions) and the abnormality patterns 824 (shown as shaded regions) from x-ray image 810, which results in a POa of 38.17%.

Figure 9:
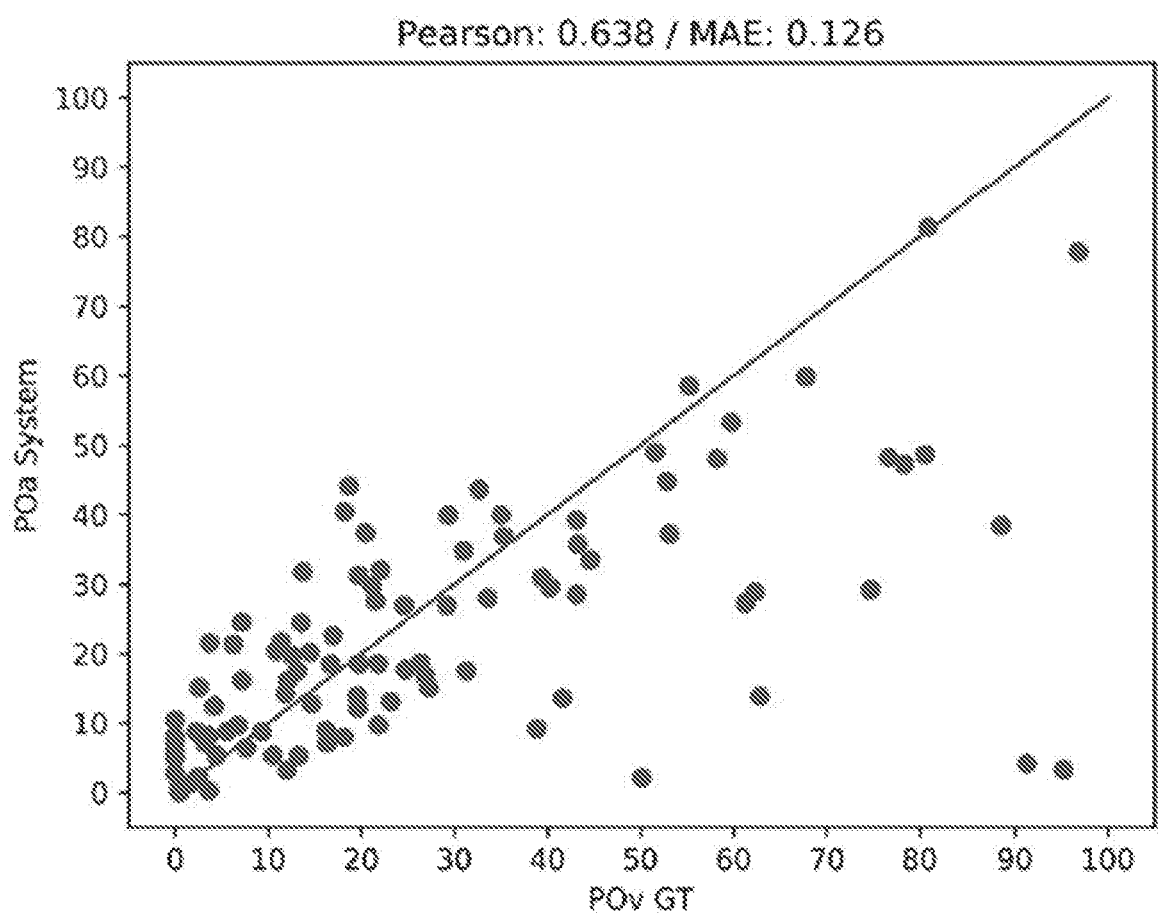
FIG. 9 shows a graph comparing POa calculated in accordance with one or more embodiments and POv for an experimental validation dataset.

Embodiments described herein were experimentally validated using a dataset comprising pairs of real x-ray images and CT images acquired from the same patient within 48 hours of each other. The POa determined from predicted segmentations from the 2D x-ray images and the POv determined from manual annotations of the 3D CT images were compared. FIG. 9 shows a graph 900 comparing the POa and POv. Each point in graph 900 represents a comparison of the POa and POv for an x-ray image and a CT image pair. As shown in graph 900, most points are within proximity to the diagonal line, representing an exact correlation between POa and POv. However, some points are well off the diagonal line. This could be attributed to a change in the patient's condition (e.g., improvement or decline) within the 48 hours of when the images were acquired, or could be attributed to limited visibility in the x-ray images.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, embodiments described herein are described with respect to methods and systems for the assessment of abnormality patterns associated with COVID-19 from x-ray images using machine learning based segmentation networks, as well as with respect to methods and systems for training a machine learning based segmentation network for the assessment of abnormality patterns associated with COVID-19. Features, advantages or alternative embodiments herein can be assigned to the other claimed objects and vice versa. In other words, claims for methods and systems for training a machine learning based network can be improved with features described or claimed in context of the methods and systems for utilizing a trained machine learning based network, and vice versa.

In particular, the trained machine learning based segmentation network of the methods and systems for the assessment of abnormality patterns associated with COVID-19 from x-ray images can be adapted by the methods and systems for training the machine learning based segmentation network for the assessment of abnormality patterns associated with COVID-19 from x-ray images. Furthermore, the input data of the trained machine learning based segmentation network can comprise advantageous features and embodiments of the training input data, and vice versa. Furthermore, the output data of the trained machine learning based segmentation network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 10:
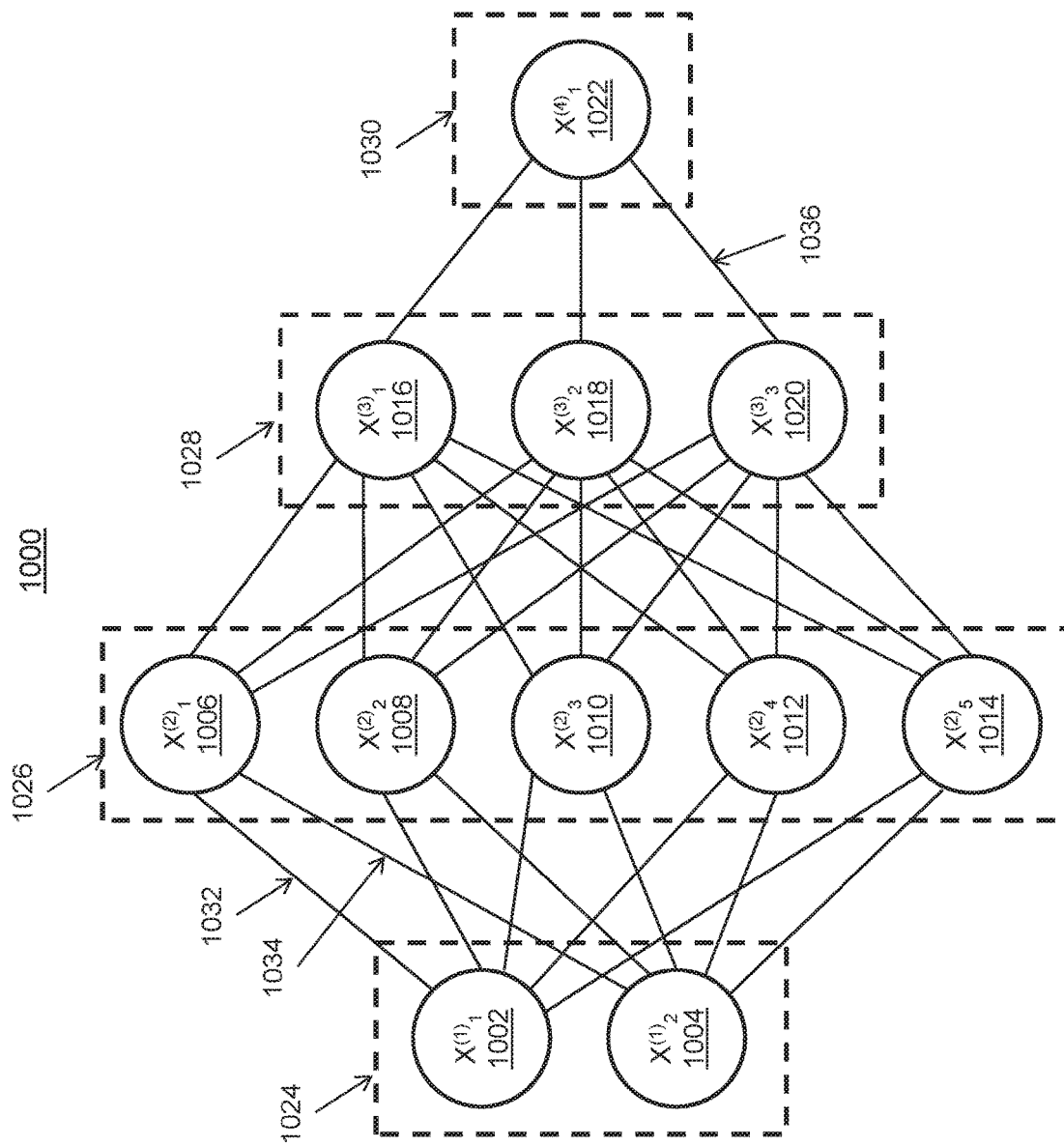
FIG. 10 shows an exemplary artificial neural network that may be used to implement one or more embodiments described herein.

FIG. 10 shows an embodiment of an artificial neural network 1000, in accordance with one or more embodiments. Alternative terms for "artificial neural network" are "neural network", "artificial neural net" or "neural net". Machine learning networks described herein, such as, e.g., lesion segmentation network 104 and lung segmentation network 110 of FIG. 1, the lung segmentation network applied at step 204 and the abnormality pattern segmentation pattern network applied at step 206 of FIG. 2, segmentation network 314 of FIG. 3, and the segmentation network trained at step 408 of FIG. 4, may be implemented using artificial neural network 1000.

The artificial neural network 1000 comprises nodes 1002-1022 and edges 1032, 1034, . . . , 1036, wherein each edge 1032, 1034, . . . , 1036 is a directed connection from a first node 1002-1022 to a second node 1002-1022. In general, the first node 1002-1022 and the second node 1002-1022 are different nodes 1002-1022, it is also possible that the first node 1002-1022 and the second node 1002-1022 are identical. For example, in FIG. 10, the edge 1032 is a directed connection from the node 1002 to the node 1006, and the edge 1034 is a directed connection from the node 1004 to the node 1006. An edge 1032, 1034, . . . , 1036 from a first node 1002-1022 to a second node 1002-1022 is also denoted as "ingoing edge" for the second node 1002-1022 and as "outgoing edge" for the first node 1002-1022.

In this embodiment, the nodes 1002-1022 of the artificial neural network 1000 can be arranged in layers 1024-1030, wherein the layers can comprise an intrinsic order introduced by the edges 1032, 1034, . . . , 1036 between the nodes 1002-1022. In particular, edges 1032, 1034, . . . , 1036 can exist only between neighboring layers of nodes. In the embodiment shown in FIG. 10, there is an input layer 1024 comprising only nodes 1002 and 1004 without an incoming edge, an output layer 1030 comprising only node 1022 without outgoing edges, and hidden layers 1026, 1028 in-between the input layer 1024 and the output layer 1030. In general, the number of hidden layers 1026, 1028 can be chosen arbitrarily. The number of nodes 1002 and 1004 within the input layer 1024 usually relates to the number of input values of the neural network 1000, and the number of nodes 1022 within the output layer 1030 usually relates to the number of output values of the neural network 1000.

In particular, a (real) number can be assigned as a value to every node 1002-1022 of the neural network 1000. Here, $x^{(n)}_i$ denotes the value of the i-th node 1002-1022 of the n-th layer 1024-1030. The values of the nodes 1002-1022 of the input layer 1024 are equivalent to the input values of the neural network 1000, the value of the node 1022 of the output layer 1030 is equivalent to the output value of the neural network 1000. Furthermore, each edge 1032, 1034, ..., 1036 can comprise a weight being a real number, in particular, the weight is a real number within the interval [−1, 1] or within the interval [0, 1]. Here, $w^{(m,n)}_{i,j}$ denotes the weight of the edge between the i-th node 1002-1022 of the m-th layer 1024-1030 and the j-th node 1002-1022 of the n-th layer 1024-1030. Furthermore, the abbreviation $w^{(n)}_{i,j}$ is defined for the weight $w^{(n,n+1)}_{i,j}$.

In particular, to calculate the output values of the neural network 1000, the input values are propagated through the neural network. In particular, the values of the nodes 1002-1022 of the (n+1)-th layer 1024-1030 can be calculated based on the values of the nodes 1002-1022 of the n-th layer 1024-1030 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 1024 are given by the input of the neural network 1000, wherein values of the first hidden layer 1026 can be calculated based on the values of the input layer 1024 of the neural network, wherein values of the second hidden layer 1028 can be calculated based in the values of the first hidden layer 1026, etc.

In order to set the values $w^{(m,n)}_{i,j}$ for the edges, the neural network 1000 has to be trained using training data. In particular, training data comprises training input data and training output data (denoted as $t_j$). For a training step, the neural network 1000 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1000 (backpropagation algorithm). In particular, the weights are changed according to $$w'^{(n)}_{i,j} = w^{(n)}_{i,j} - \gamma \cdot \delta_j^{(n)} \cdot x_i^{(n)}$$

wherein γ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 1030, wherein f' is the first derivative of the activation function, and $y^{(n+1)}_j$ is the comparison training value for the j-th node of the output layer 1030.

Figure 11:
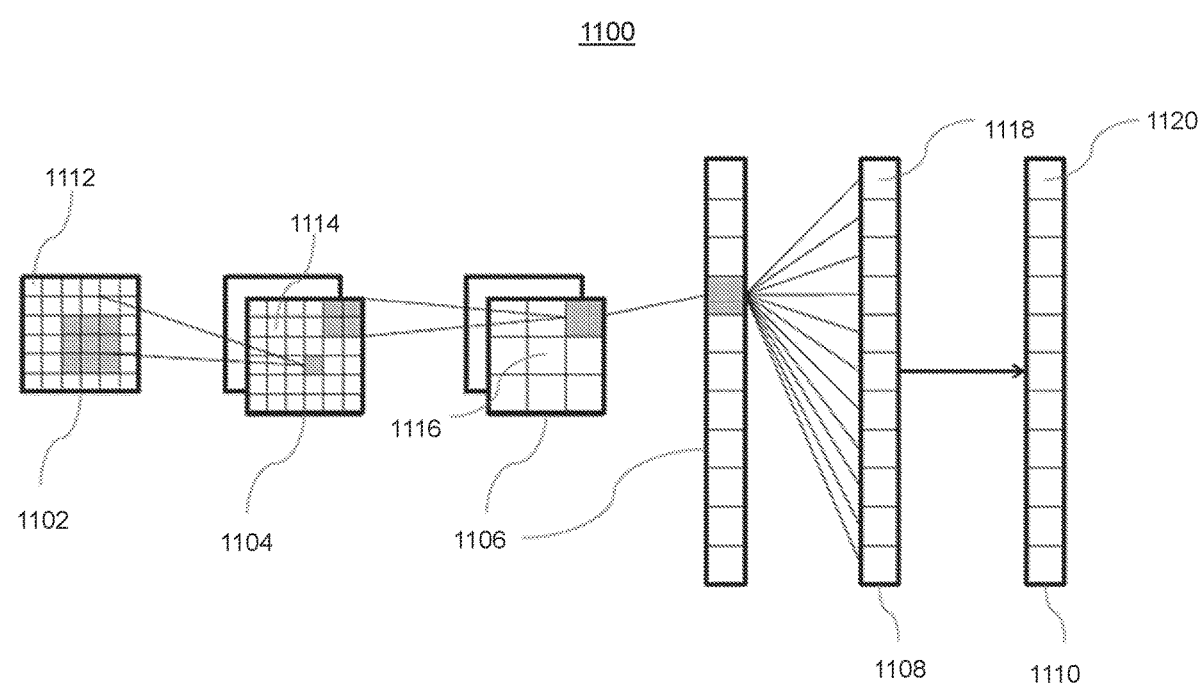
FIG. 11 shows a convolutional neural network that may be used to implement one or more embodiments described herein.

FIG. 11 shows a convolutional neural network 1100, in accordance with one or more embodiments. Machine learning networks described herein, such as, e.g., lesion segmentation network 104 and lung segmentation network 110 of FIG. 1, the lung segmentation network applied at step 204 and the abnormality pattern segmentation pattern network applied at step 206 of FIG. 2, segmentation network 314 of FIG. 3, and the segmentation network trained at step 408 of FIG. 4, may be implemented using convolutional neural network 1100.

In the embodiment shown in FIG. 11, the convolutional neural network comprises 1100 an input layer 1102, a convolutional layer 1104, a pooling layer 1106, a fully connected layer 1108, and an output layer 1110. Alternatively, the convolutional neural network 1100 can comprise several convolutional layers 1104, several pooling layers 1106, and several fully connected layers 1108, as well as other types of layers. The order of the layers can be chosen arbitrarily, usually fully connected layers 1108 are used as the last layers before the output layer 1110.

In particular, within a convolutional neural network 1100, the nodes 1112-1120 of one layer 1102-1110 can be considered to be arranged as a d-dimensional matrix or as a d-dimensional image. In particular, in the two-dimensional case the value of the node 1112-1120 indexed with i and j in the n-th layer 1102-1110 can be denoted as $x^{(n)}_{[i,j]}$. However, the arrangement of the nodes 1112-1120 of one layer 1102-1110 does not have an effect on the calculations executed within the convolutional neural network 1100 as such, since these are given solely by the structure and the weights of the edges.

In particular, a convolutional layer 1104 is characterized by the structure and the weights of the incoming edges forming a convolution operation based on a certain number of kernels. In particular, the structure and the weights of the incoming edges are chosen such that the values $x^{(n)}_k$ of the nodes 1114 of the convolutional layer 1104 are calculated as a convolution $x^{(n)}_k = K_k * x^{(n-1)}$ based on the values $x^{(n-1)}$ of the nodes 1112 of the preceding layer 1102, where the convolution * is defined in the two-dimensional case as $$x_k^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 1112-1118 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1112-1120 in the respective layer 1102-1110. In particular, for a convolutional layer 1104, the number of nodes 1114 in the convolutional layer is equivalent to the number of nodes 1112 in the preceding layer 1102 multiplied with the number of kernels.

If the nodes 1112 of the preceding layer 1102 are arranged as a d-dimensional matrix, using a plurality of kernels can be interpreted as adding a further dimension (denoted as "depth" dimension), so that the nodes 1114 of the convolutional layer 1114 are arranged as a (d+1)-dimensional matrix. If the nodes 1112 of the preceding layer 1102 are already arranged as a (d+1)-dimensional matrix comprising a depth dimension, using a plurality of kernels can be interpreted as expanding along the depth dimension, so that the nodes 1114 of the convolutional layer 1104 are arranged also as a (d+1)-dimensional matrix, wherein the size of the (d+1)-dimensional matrix with respect to the depth dimension is by a factor of the number of kernels larger than in the preceding layer 1102.

The advantage of using convolutional layers 1104 is that spatially local correlation of the input data can exploited by enforcing a local connectivity pattern between nodes of adjacent layers, in particular by each node being connected to only a small region of the nodes of the preceding layer.

In embodiment shown in FIG. 11, the input layer 1102 comprises 36 nodes 1112, arranged as a two-dimensional 6×6 matrix. The convolutional layer 1104 comprises 72 nodes 1114, arranged as two two-dimensional 6×6 matrices, each of the two matrices being the result of a convolution of the values of the input layer with a kernel. Equivalently, the nodes 1114 of the convolutional layer 1104 can be interpreted as arranges as a three-dimensional 6×6×2 matrix, wherein the last dimension is the depth dimension.

A pooling layer 1106 can be characterized by the structure and the weights of the incoming edges and the activation function of its nodes 1116 forming a pooling operation based on a non-linear pooling function f. For example, in the two dimensional case the values $x^{(n)}$ of the nodes 1116 of the pooling layer 1106 can be calculated based on the values $x^{(n-1)}$ of the nodes 1114 of the preceding layer 1104 as $$x^{(n)}[i,j]=f(x^{(n-1)}[id_1,jd_2], \ldots, x^{(n-1)}[id_1+id_1-1, jd_2+d_2-1])$$

In other words, by using a pooling layer 1106, the number of nodes 1114, 1116 can be reduced, by replacing a number d1·d2 of neighboring nodes 1114 in the preceding layer 1104 with a single node 1116 being calculated as a function of the values of said number of neighboring nodes in the pooling layer. In particular, the pooling function f can be the max-function, the average or the L2-Norm. In particular, for a pooling layer 1106 the weights of the incoming edges are fixed and are not modified by training.

The advantage of using a pooling layer 1106 is that the number of nodes 1114, 1116 and the number of parameters is reduced. This leads to the amount of computation in the network being reduced and to a control of overfitting.

In the embodiment shown in FIG. 11, the pooling layer 1106 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1108 can be characterized by the fact that a majority, in particular, all edges between nodes 1116 of the previous layer 1106 and the nodes 1118 of the fully-connected layer 1108 are present, and wherein the weight of each of the edges can be adjusted individually.

In this embodiment, the nodes 1116 of the preceding layer 1106 of the fully-connected layer 1108 are displayed both as two-dimensional matrices, and additionally as non-related nodes (indicated as a line of nodes, wherein the number of nodes was reduced for a better presentability). In this embodiment, the number of nodes 1118 in the fully connected layer 1108 is equal to the number of nodes 1116 in the preceding layer 1106. Alternatively, the number of nodes 1116, 1118 can differ.

Furthermore, in this embodiment, the values of the nodes 1120 of the output layer 1110 are determined by applying the Softmax function onto the values of the nodes 1118 of the preceding layer 1108. By applying the Softmax function, the sum the values of all nodes 1120 of the output layer 1110 is 1, and all values of all nodes 1120 of the output layer are real numbers between 0 and 1.

A convolutional neural network 1100 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1100 can be trained based on the backpropagation algorithm. For preventing overfitting, methods of regularization can be used, e.g. dropout of nodes 1112-1120, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another datasets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2 and 4. Certain steps or functions of the methods and workflows described herein, including one or more of the steps or functions of FIGS. 2 and 4, may be performed by a server or by another processor in a network-based cloud-computing system. Certain steps or functions of the methods and workflows described herein, including one or more of the steps of FIGS. 2 and 4, may be performed by a client computer in a network-based cloud computing system. The steps or functions of the methods and workflows described herein, including one or more of the steps of FIGS. 2 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 12:
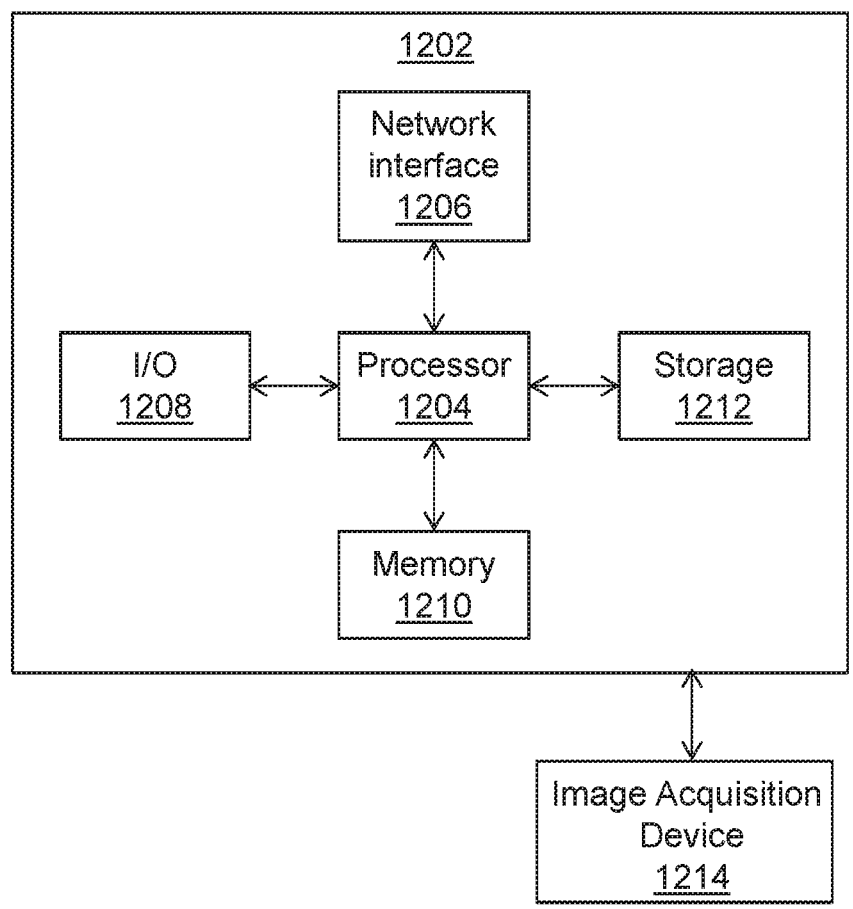
FIG. 12 shows a high-level block diagram of a computer that may be used to implement one or more embodiments described herein.

A high-level block diagram of an example computer 1202 that may be used to implement systems, apparatus, and methods described herein is depicted in FIG. 12. Computer 1202 includes a processor 1204 operatively coupled to a data storage device 1212 and a memory 1210. Processor 1204 controls the overall operation of computer 1202 by executing computer program instructions that define such operations. The computer program instructions may be stored in data storage device 1212, or other computer readable medium, and loaded into memory 1210 when execution of the computer program instructions is desired. Thus, the method and workflow steps or functions of FIGS. 2 and 4 can be defined by the computer program instructions stored in memory 1210 and/or data storage device 1212 and controlled by processor 1204 executing the computer program instructions. For example, the computer program instructions can be implemented as computer executable code programmed by one skilled in the art to perform the method and workflow steps or functions of FIGS. 2 and 4. Accordingly, by executing the computer program instructions, the processor 1204 executes the method and workflow steps or functions of FIGS. 2 and 4. Computer 1202 may also include one or more network interfaces 1206 for communicating with other devices via a network. Computer 1202 may also include one or more input/output devices 1208 that enable user interaction with computer 1202 (e.g., display, keyboard, mouse, speakers, buttons, etc.).

Processor 1204 may include both general and special purpose microprocessors, and may be the sole processor or one of multiple processors of computer 1202. Processor 1204 may include one or more central processing units (CPUs), for example. Processor 1204, data storage device 1212, and/or memory 1210 may include, be supplemented by, or incorporated in, one or more application-specific integrated circuits (ASICs) and/or one or more field programmable gate arrays (FPGAs).

Data storage device 1212 and memory 1210 each include a tangible non-transitory computer readable storage medium. Data storage device 1212, and memory 1210, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1208 may include peripherals, such as a printer, scanner, display screen, etc. For example, input/output devices 1208 may include a display device such as a cathode ray tube (CRT) or liquid crystal display (LCD) monitor for displaying information to the user, a keyboard, and a pointing device such as a mouse or a trackball by which the user can provide input to computer 1202.

An image acquisition device 1214 can be connected to the computer 1202 to input image data (e.g., medical images) to the computer 1202. It is possible to implement the image acquisition device 1214 and the computer 1202 as one device. It is also possible that the image acquisition device 1214 and the computer 1202 communicate wirelessly through a network. In a possible embodiment, the computer 1202 can be located remotely with respect to the image acquisition device 1214.

Any or all of the systems and apparatus discussed herein, including lesion segmentation network 104 and lung segmentation network 110 of FIG. 1, the lung segmentation network applied at step 204 and the abnormality pattern segmentation pattern network applied at step 206 of FIG. 2, segmentation network 314 of FIG. 3, and the segmentation network trained at step 408 of FIG. 4, may be implemented using one or more computers such as computer 1202.

One skilled in the art will recognize that an implementation of an actual computer or computer system may have other structures and may contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method, comprising:
receiving an input medical image in a first modality;
segmenting lungs from the input medical image using a trained lung segmentation network;
segmenting abnormality patterns associated with a disease from the input medical image using a trained abnormality pattern segmentation network; and
determining an assessment of the disease based on the segmented lungs and the segmented abnormality patterns,
wherein the trained lung segmentation network and the trained abnormality pattern segmentation network are trained based on 1) synthesized images in the first modality generated from training images of an anatomical object in a second modality and 2) target segmentation masks for the synthesized images, the target segmentation masks generated by:
projecting regions of the training images within their corresponding training segmentation masks to a two dimensional mask, and
assigning each pixel in the two dimensional mask a value corresponding to a sum of intensity values of voxels in the training images that are within the anatomical object and penetrated by the projection for that pixel.

2. The computer implemented method of claim 1, wherein the disease is COVID-19 (coronavirus disease 2019) and the abnormality patterns comprise at least one of GGO (ground glass opacity), consolidation, and crazy-paving pattern.

3. The computer implemented method of claim 1, further comprising training at least one of the lung segmentation network and the abnormality pattern segmentation network by:
receiving the training images of the anatomical object of interest in the second modality and the training segmentation masks for the training images;
generating the synthesized images in the first modality based on the training images;
generating the target segmentation masks for the synthesized images based on the training segmentation masks; and
training the at least one of the lung segmentation network and the abnormality pattern segmentation network based on the synthesized images and the target segmentation masks.

4. The computer implemented method of claim 1, wherein the target segmentation masks are further generated by generating target segmentation masks for the synthesized images based on the training segmentation masks further comprises:
comparing the value of each pixel in the two dimensional mask to a threshold value; and
assigning each pixel in the two dimensional mask a final value based on the comparing.

5. The computer implemented method of claim 1, wherein determining an assessment of the disease based on the segmented lungs and the segmented abnormality patterns comprises:
calculating a percent of affected lung area metric based on an area of the lungs determined from the segmented lungs and an area of the abnormality patterns determined from the segmented abnormality patterns.

6. The computer implemented method of claim 1, further comprising:
detecting the disease in the input medical image based on the assessment of the disease.

7. The computer implemented method of claim 1, further comprising:
predicting an evolution of the disease based on the assessment of the disease and an assessment of the disease determined for a different point in time.

8. The computer implemented method of claim 1, wherein the first modality is x-ray and the second modality is CT (computed tomography).

9. An apparatus comprising:
means for receiving an input medical image in a first modality;
means for segmenting lungs from the input medical image using a trained lung segmentation network;
means for segmenting abnormality patterns associated with a disease from the input medical image using a trained abnormality pattern segmentation network; and
means for determining an assessment of the disease based on the segmented lungs and the segmented abnormality patterns,
wherein the trained lung segmentation network and the trained abnormality pattern segmentation network are trained based on 1) synthesized images in the first modality generated from training images of an anatomical object in a second modality and 2) target segmentation masks for the synthesized images, the target segmentation masks generated by:
projecting regions of the training images within their corresponding training segmentation masks to a two dimensional mask, and
assigning each pixel in the two dimensional mask a value corresponding to a sum of intensity values of voxels in the training images that are within the anatomical object and penetrated by the projection for that pixel.

10. The apparatus of claim 9, wherein the disease is COVID-19 (coronavirus disease 2019) and the abnormality patterns comprise at least one of GGO (ground glass opacity), consolidation, and crazy-paving pattern.

11. The apparatus of claim 9, further comprising means for training at least one of the lung segmentation network and the abnormality pattern segmentation network by:
means for receiving the training images of the anatomical object of interest in the second modality and the training segmentation masks for the training images;
means for generating the synthesized images in the first modality based on the training images;
means for generating the target segmentation masks for the synthesized images based on the training segmentation masks; and
means for training the at least one of the lung segmentation network and the abnormality pattern segmentation network based on the synthesized images and the target segmentation masks.

12. The apparatus of claim 9, wherein the target segmentation masks are further generated by the means for generating target segmentation masks for the synthesized images based on the training segmentation masks further comprises:
means for comparing the value of each pixel in the two dimensional mask to a threshold value; and
means for assigning each pixel in the two dimensional mask a final value based on the comparing.

13. The apparatus of claim 9, further comprising:
means for detecting the disease in the input medical image based on the assessment of the disease.

14. The apparatus of claim 9, wherein the means for determining an assessment of the disease based on the segmented lungs and the segmented abnormality patterns comprises:

means for calculating a percent of affected lung area metric based on an area of the lungs determined from the segmented lungs and an area of the abnormality patterns determined from the segmented abnormality patterns.

15. The apparatus of claim 9, further comprising:
means for predicting an evolution of the disease based on the assessment of the disease and an assessment of the disease determined for a different point in time.

16. The apparatus of claim 9, wherein the first modality is x-ray and the second modality is CT (computed tomography).

17. A non-transitory computer readable medium storing computer program instructions, the computer program instructions when executed by a processor cause the processor to perform operations comprising:
receiving an input medical image in a first modality;
segmenting lungs from the input medical image using a trained lung segmentation network;
segmenting abnormality patterns associated with a disease from the input medical image using a trained abnormality pattern segmentation network; and
determining an assessment of the disease based on the segmented lungs and the segmented abnormality patterns,
wherein the trained lung segmentation network and the trained abnormality pattern segmentation network are trained based on 1) synthesized images in the first modality generated from training images of an anatomical object in a second modality and 2) target segmentation masks for the synthesized images, the target segmentation masks generated by:
projecting regions of the training images within their corresponding training segmentation masks to a two dimensional mask, and
assigning each pixel in the two dimensional mask a value corresponding to a sum of intensity values of voxels in the training images that are within the anatomical object and penetrated by the projection for that pixel.

18. The non-transitory computer readable medium of claim 17, wherein the disease is COVID-19 (coronavirus disease 2019) and the abnormality patterns comprise at least one of GGO (ground glass opacity), consolidation, and crazy-paving pattern.

19. The non-transitory computer readable medium of claim 17, further comprising training at least one of the lung segmentation network and the abnormality pattern segmentation network by:
receiving the training images of the anatomical object of interest in the second modality and the training segmentation masks for the training images;
generating the synthesized images in the first modality based on the training images;
generating the target segmentation masks for the synthesized images based on the training segmentation masks; and
training the at least one of the lung segmentation network and the abnormality pattern segmentation network based on the synthesized images and the target segmentation masks.

20. The non-transitory computer readable medium of claim 17, wherein the target segmentation masks are further generated by generating target segmentation masks for the synthesized images based on the training segmentation masks further comprises:
comparing the value of each pixel in the two dimensional mask to a threshold value; and
assigning each pixel in the two dimensional mask a final value based on the comparing.

21. The non-transitory computer readable medium of claim 17, wherein the first modality is x-ray and the second modality is CT (computed tomography).

22. The non-transitory computer readable of claim 17, the operations further comprising:
predicting an evolution of the disease based on the assessment of the disease and an assessment of the disease determined for a different point in time.

23. The non-transitory computer readable medium of claim 17, wherein determining an assessment of the disease based on the segmented lungs and the segmented abnormality patterns comprises:
calculating a percent of affected lung area metric based on an area of the lungs determined from the segmented lungs and an area of the abnormality patterns determined from the segmented abnormality patterns.

24. The non-transitory computer readable medium of claim 17, the operations further comprising:
detecting the disease in the input medical image based on the assessment of the disease.

* * * * *